(12) United States Patent
Dorman

(10) Patent No.: US 11,123,111 B2
(45) Date of Patent: Sep. 21, 2021

(54) CERVICAL LINK SYSTEM

(71) Applicant: Scapa Flow, LLC, Midland, TX (US)

(72) Inventor: John Dorman, Midland, TX (US)

(73) Assignee: Scapa Flow, LLC, Midland, TX (US)

( * ) Notice: Subject to any disclaimer, the term of this patent is extended or adjusted under 35 U.S.C. 154(b) by 65 days.

(21) Appl. No.: 16/292,217

(22) Filed: Mar. 4, 2019

(65) Prior Publication Data

US 2019/0192195 A1 Jun. 27, 2019

Related U.S. Application Data

(63) Continuation of application No. 12/729,990, filed on Mar. 23, 2010, now Pat. No. 10,219,842.

(51) Int. Cl.
*A61B 17/70* (2006.01)

(52) U.S. Cl.
CPC ...... *A61B 17/7059* (2013.01); *A61B 17/7002* (2013.01); *A61B 17/7032* (2013.01); *A61B 17/7041* (2013.01); *A61B 17/7044* (2013.01)

(58) Field of Classification Search
CPC ............ A61B 17/70–7046; A61B 17/80–8095
See application file for complete search history.

(56) References Cited

U.S. PATENT DOCUMENTS

| | | | |
|---|---|---|---|
| 5,397,363 A | 3/1995 | Gelbard | |
| 5,582,612 A * | 12/1996 | Lin | A61B 17/7044 606/250 |
| 5,704,936 A * | 1/1998 | Mazel | A61B 17/7044 606/254 |
| 5,800,435 A * | 9/1998 | Errico | A61B 17/7007 606/261 |

(Continued)

FOREIGN PATENT DOCUMENTS

| | | |
|---|---|---|
| FR | 2656214 | 6/1991 |
| WO | WO-9508298 | 3/1995 |

(Continued)

OTHER PUBLICATIONS

International Preliminary Report on Patentability for PCT Application No. PCT/US2011/029651, dated Oct. 4, 2012 (8 pages).

(Continued)

*Primary Examiner* — Eduardo C Robert
*Assistant Examiner* — Steven J Cotroneo
(74) *Attorney, Agent, or Firm* — Foley & Lardner LLP

(57) ABSTRACT

An adjustable cervical link system that includes a plurality of cervical links for adjustable fixation to articles of a patient's cervical spine, and a connecting assembly having a generally rectangular loop shape defining a substantially open interior therebetween. Each cervical link has a plurality of circular holes each arranged to receive a screw thereby securing the cervical link to the respective article of a patient's cervical spine at a bottom portion of the cervical link. Each cervical link has a plurality of recessed portion along a top portion of the cervical link. Each recessed portion has a generally U-shaped cross-section formed by a bottom portion and a pair of spaced apart side walls. The connecting assembly is arranged to be placed in and frictionally engage the U-shaped cross-section of the recessed portions.

17 Claims, 2 Drawing Sheets

(56) References Cited

U.S. PATENT DOCUMENTS

| | | | | |
|---|---|---|---|---|
| 5,843,082 A * | 12/1998 | Yuan | A61B 17/7044 | 606/250 |
| 6,117,135 A * | 9/2000 | Schlapfer | A61B 17/7044 | 606/250 |
| 6,206,879 B1 * | 3/2001 | Marnay | A61B 17/7035 | 606/53 |
| 6,296,643 B1 * | 10/2001 | Hopf | A61B 17/70 | 606/263 |
| 6,702,817 B2 * | 3/2004 | Beger | A61B 17/1671 | 606/294 |
| 6,786,907 B2 * | 9/2004 | Lange | A61B 17/7037 | 606/250 |
| 6,872,210 B2 * | 3/2005 | Hearn | A61B 17/8009 | 606/71 |
| 7,651,497 B2 * | 1/2010 | Michelson | A61B 17/1604 | 606/247 |
| 7,666,185 B2 * | 2/2010 | Ryan | A61B 17/7059 | 606/71 |
| 7,803,174 B2 * | 9/2010 | Denis | A61B 17/7035 | 606/250 |
| 8,034,085 B2 * | 10/2011 | Slivka | A61B 17/7044 | 606/266 |
| 8,442,621 B2 | 5/2013 | Gorek et al. | | |
| 9,119,572 B2 | 9/2015 | Gorek et al. | | |
| 9,585,700 B2 | 3/2017 | Wehrle et al. | | |
| 10,064,687 B2 | 9/2018 | Haimerl et al. | | |
| 10,342,619 B2 | 7/2019 | Bracke et al. | | |
| 10,561,466 B2 | 2/2020 | Hedblom et al. | | |
| 10,602,114 B2 | 3/2020 | Casas | | |
| 2002/0193795 A1 * | 12/2002 | Gertzbein | A61B 17/7044 | 606/269 |
| 2003/0045875 A1 * | 3/2003 | Bertranou | A61B 17/7007 | 606/261 |
| 2003/0171752 A1 * | 9/2003 | Assaker | A61B 17/7037 | 606/250 |
| 2003/0220642 A1 * | 11/2003 | Freudiger | A61B 17/7005 | 606/254 |
| 2004/0116931 A1 * | 6/2004 | Carlson | A61B 17/7011 | 606/70 |
| 2005/0228382 A1 | 10/2005 | Richelsoph et al. | | |
| 2006/0079901 A1 * | 4/2006 | Ryan | A61B 17/8047 | 606/70 |
| 2006/0206114 A1 * | 9/2006 | Ensign | A61B 17/7037 | 606/278 |
| 2009/0281579 A1 * | 11/2009 | Weaver | A61B 17/7037 | 606/286 |
| 2010/0004693 A1 | 1/2010 | Miller et al. | | |
| 2018/0303559 A1 | 10/2018 | Shepherd et al. | | |
| 2018/0310956 A1 | 11/2018 | Polster | | |
| 2019/0046278 A1 | 2/2019 | Steinle et al. | | |
| 2019/0388173 A1 | 12/2019 | Pak et al. | | |

FOREIGN PATENT DOCUMENTS

| | | |
|---|---|---|
| WO | WO-2008014477 | 1/2008 |
| WO | WO-2010004613 | 1/2010 |

OTHER PUBLICATIONS

International Search Report for Co-Pending PCT Application No. PCT/US11/29651 dated Jun. 2, 2011.

Written Opinion for Co-Pending PCT Application No. PCT/US11/29651 dated Jun. 2, 2011.

* cited by examiner

CERVICAL LINK SYSTEM

CROSS-REFERENCE TO RELATED APPLICATIONS

Pursuant to pre-AIA 35 U.S.C. § 119, this application is a continuation of and claims the benefit of U.S. patent application Ser. No. 12/729,990, entitled "Cervical Link System," filed Mar. 23, 2010, and naming John Dorman as inventor, the disclosure of which is incorporated herein by reference in its entirety.

FIELD

This invention is related in general to the field of cervical spine devices. More particularly, the invention is related to cervical link system for the cervical spine.

BACKGROUND

The cervical spine begins at the base of the skull. Seven vertebrae make up the cervical spine with eight pairs of cervical nerves. The individual cervical vertebrae are abbreviated as C1-C7. The related cervical nerves are abbreviated as C1-C8.

Patients who have herniated cervical discs often require surgery. The standard operation for a patient with a herniated cervical disc is an anterior cervical discectomy and fusion (ACDF) operation. ACDF operations have been performed since the 1950s. Back then, the disc was removed from the patient and a bone graft inserted. Later, in the 1970s, surgeons began to use a cervical plate in addition to a bone graft.

There currently exist numerous deficiencies in cervical spine devices that are known in the prior art. For instance, it is difficult to achieve optimum placement of cervical plates due to variations in the size of vertebral bodies in a patient. For example, C5 may be larger than C6, or the C5-C6 disc space may be larger or smaller than the C6-C7 disc space. Further, the insertion of cervical plates that are known in the prior art through small surgical openings is often difficult due to the size of the cervical plate. This is especially true for large cervical plates that are used in multi-level procedures.

Thus, as noted above, there currently exist numerous deficiencies in cervical spine devices that are known in the prior art.

SUMMARY

Accordingly, one aspect of the present invention is to provide an adjustable cervical link system that includes a plurality of cervical links for adjustable fixation to articles of a patient's cervical spine, and a connecting assembly having a generally rectangular loop shape defining a substantially open interior therebetween. Each cervical link has a plurality of circular holes each arranged to receive a screw thereby securing the cervical link to the respective article of a patient's cervical spine at a bottom portion of the cervical link. Each cervical link has a plurality of recessed portion along a top portion of the cervical link. Each recessed portion has a generally U-shaped cross-section formed by a bottom portion and a pair of spaced apart side walls. The connecting assembly is arranged to be placed in and frictionally engage the U-shaped cross-section of the recessed portions.

Another aspect of the present invention is to provide an adjustable cervical link system that includes a plurality of cervical links for adjustable fixation to articles of a patient's cervical spine and a connecting assembly having a generally rectangular loop shape defining a substantially open interior therebetween. Each cervical link has a plurality of circular holes each arranged to receive a screw thereby securing the cervical link to the respective article of a patient's cervical spine at a bottom portion of the cervical link. Each cervical link has an open recessed slot along a top portion of the cervical link, each open recessed slot is defined by a bottom portion and a pair of spaced apart semi-elliptical side walls. A rotatable semi-elliptical adjustment member is positioned within the open recessed slot. The connecting assembly is arranged to be placed in the open recessed slot and to be positioned between the spaced apart semi-elliptical side walls and the rotatable semi-elliptical adjustment member when the rotatable semi-elliptical adjustment member is rotated into a locked position.

BRIEF DESCRIPTION OF THE DRAWINGS

A more complete appreciation of the present invention and many of the attendant advantages thereof will be readily obtained as the same becomes better understood by reference to the following detailed description when considered in conjunction with the accompanying drawings, wherein.

DETAILED DESCRIPTION

Figure 1:
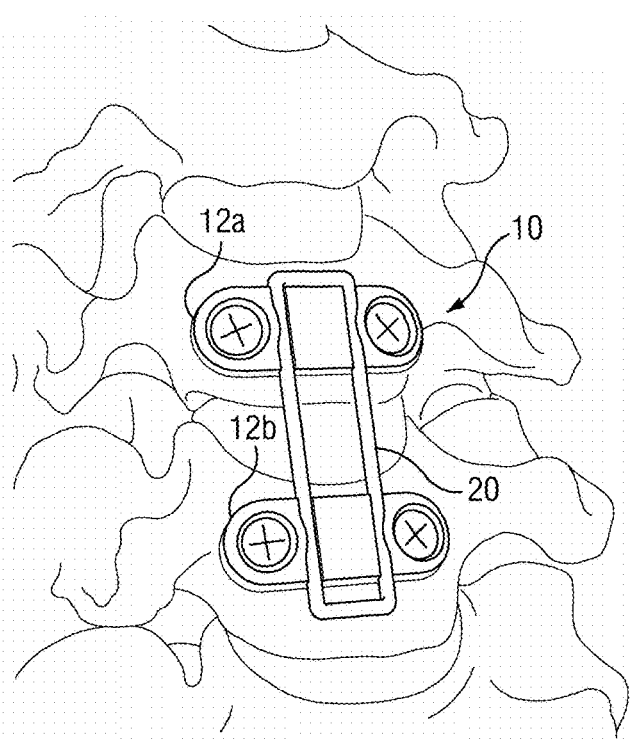
FIG. 1 is a front view of a cervical link system secured to a patient's cervical spine according to an embodiment of the present invention.
Figure 4:
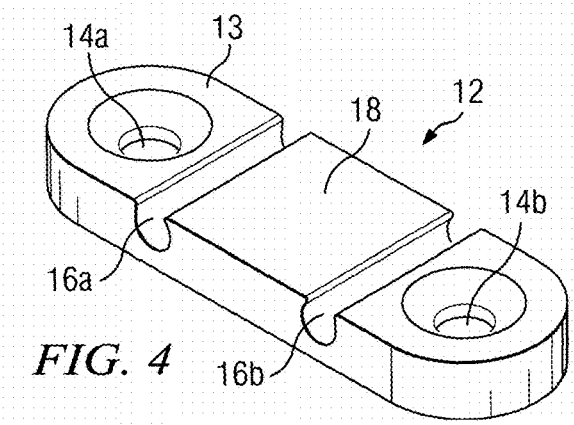
FIG. 4 is a front view of a section of a portion of the cervical link system according to an embodiment of the present invention.

Referring now to the drawings, wherein like reference numerals designate identical or corresponding parts throughout the several views, preferred embodiments of the present invention are described.

It is difficult to achieve optimum placement of cervical plates that are known in the prior art due to variations in the size of the vertebral bodies in a patient. For example, C5 may be larger than C6, or the C5-C6 disc space may be larger or smaller than the C6-C7 disc space. Further, the insertion of cervical plates that are known in the prior art through small surgical openings is often difficult due to the size of the cervical plate. This is especially true for large cervical plates that are used in multi-level procedures. The present invention, known as the cervical link system, overcomes these obstacles by allowing each cervical link to be separately secured to a respective vertebral body of a patient. After the cervical links have been secured, the cervical links are then linked together by means of adjustable arms (or connecting assembly) interconnecting the cervical links. The present invention allows for easier placement as the cervical links and adjustable arms (or connecting assembly) due to their small size, which is smaller than cervical plates that are known in the prior art. The adjustable arms (or connecting assembly) interconnecting the cervical links of the present invention allow for possible differences in the size of the vertebral bodies and/or disc spaces in the patient.

Figure 2:
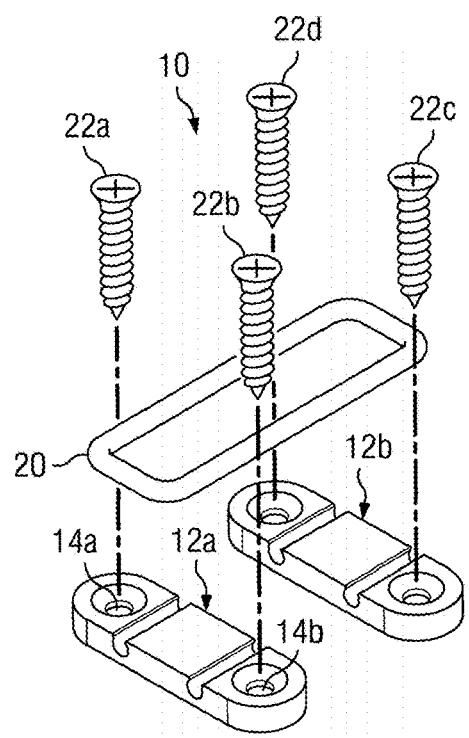
FIG. 2 is an exploded front view of the cervical link system according to an embodiment of the present invention.

Referring now to FIG. 2, an exploded front view of the cervical link system 10 according to an embodiment of the present invention is shown. As shown in FIG. 1, the cervical link system 10 serves for adjustably connecting vertebral bodies of a patient.

The cervical link system 10 includes one or more cervical links (12a, 12b) and a connecting assembly 20. The connecting assembly 20 is a tubular bar or arm having a generally rectangular loop shape defining an open interior therebetween. Optionally, the connecting assembly 20 may have a generally circular loop shape. Further, the connecting assembly 20 may be two unconnected parallel spaced bars or arms.

Each cervical link (12a, 12b) includes a top portion 13 having circular holes (14a, 14b), and a plurality of circular recessed portions (16a, 16b). Each cervical link (12a, 12b) is secured to a vertebral body of a patient by one or more screws (22a-22d) or the like which are projected through the circular holes (14a, 14b). The connecting assembly 20 is arranged to be inserted into circular recessed portions (16a, 16b) of each cervical link (12a, 12b).

Figure 3:
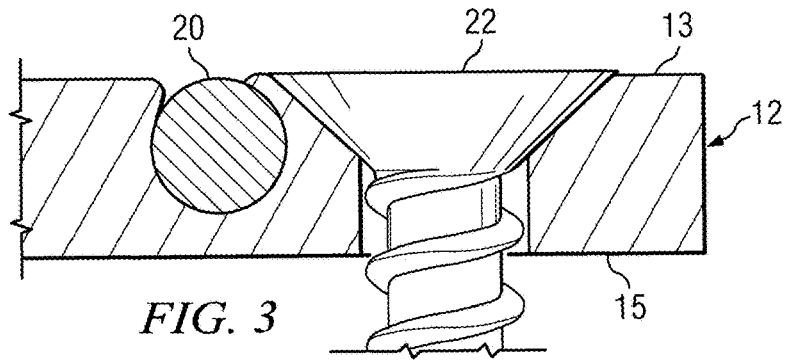
FIG. 3 is an cutaway cross-section view of a portion of the cervical link system according to an embodiment of the present invention.

As shown in FIG. 3, each circular recessed portion (16a, 16b) generally has a semi-circular cross-section configuration defined by side and bottom portions and a generally open top portion along a longitudinal center axis. The generally semi-circular cross-section of the circular recessed portions (16a, 16b) is configured and sized such that the connecting assembly 20 frictionally engages the semi-circular cross-section of the circular recessed portions (16a, 16b) when the connecting assembly 20 is inserted into the circular recessed portions (16a, 16b) of each cervical link (12a, 12b). According to at least one embodiment, of the opening of the top portion of the circular recessed portions (16a, 16b) is slightly less the width of the connecting assembly 20 and configured to deflect slightly during insertion of the connecting assembly 20 and to therefore lock in place the connecting assembly 20 within the circular recessed portions (16a, 16b).

It is of course to be understood that the present invention is not limited to the above identified connecting components and that other connecting components may be used within the scope of the present invention. Each of the cervical link system 10 components may be made from any material. In one embodiment, the components of the cervical link system 10 are made from non-corrosive metal formed from pressure casting or stamping. In another embodiment, the components of the cervical link system 10 are made from plastic, composite, or other suitable material that can be inserted into the body of a patient for an extended period of time without causing medical complications due to composition of such material.

Figure 5:
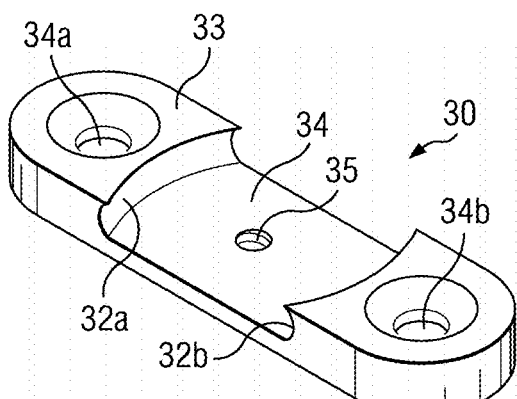
FIG. 5 is a front view of a section of a portion of the cervical link system according to an alternate embodiment of the present invention.
Figure 6:
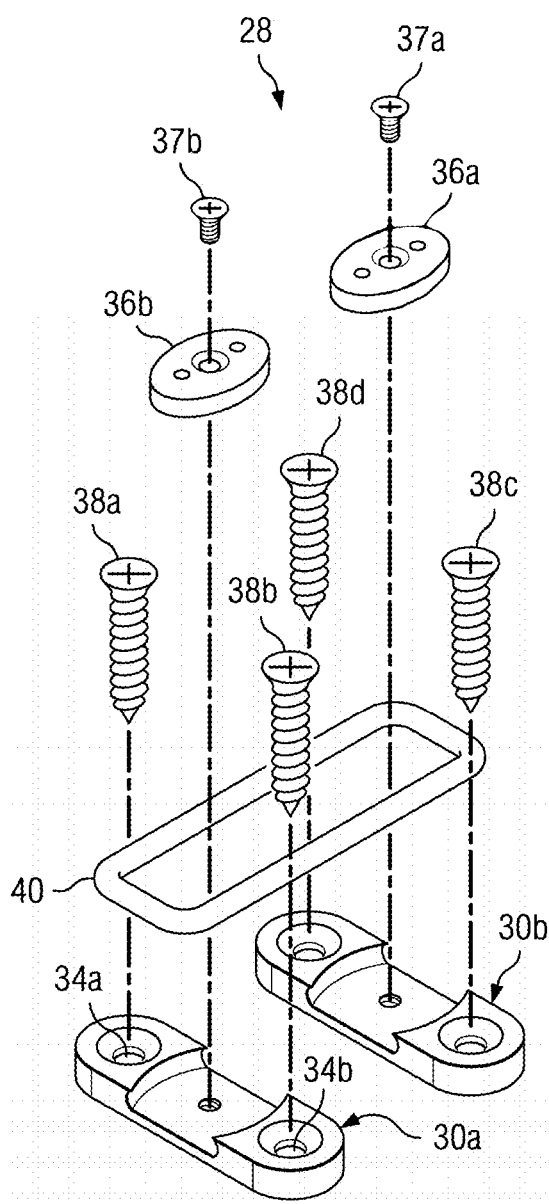
FIG. 6 is an exploded front view of the cervical link system according to an alternate embodiment of the present invention.
Figure 7:
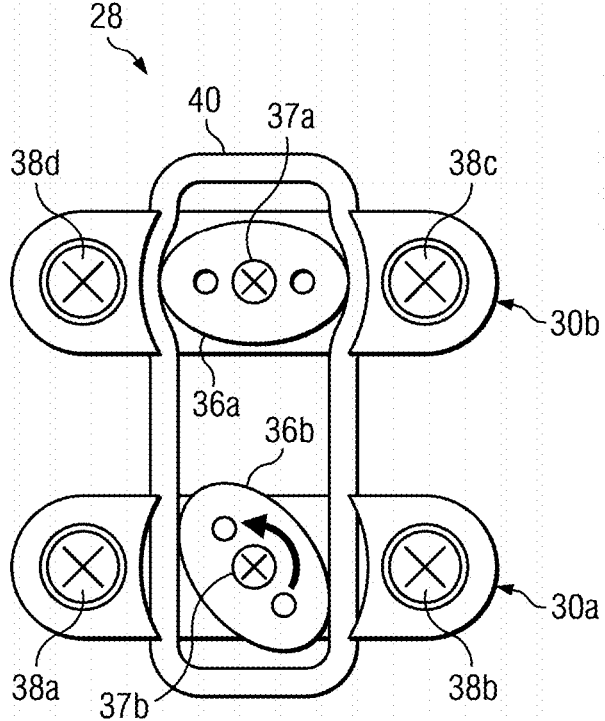
FIG. 7 is a top view of the cervical link system according to an alternate embodiment of the present invention.

Referring now to FIGS. 5-7, a cervical link system 28 according to an alternate embodiment of the present invention is shown. According to this alternate embodiment, the cervical link system 28 includes one or more cervical links (30a, 30b) and a connecting assembly 40. The connecting assembly 40 is a tubular bar or arm having a generally rectangular loop shape defining a substantially open interior therebetween. Optionally, the connecting assembly 40 may have a generally circular loop shape.

Each cervical link (30a, 30b) includes a top portion 33 having circular holes (34a, 34b), and a center recessed portion 34 (or slot) defined by two semi-elliptical side walls and a bottom portion. A semi-elliptical movable locking member 36 is positioned substantially in the center of the center recessed portion 34 by means of any means known in the art, including without limitation, a screw, bar, pin, bolt or the like (37a, 37b). Each semi-elliptical movable locking member (36a, 36b) is rotatably secured to the respective cervical link (30a, 30b) by a screw, bar, pin, bolt or the like (37a, 37b) or the like which are projected through circular holes (35) of the respective cervical link (30a, 30b). It is to be understood that the screws (37a, 37b) and the respective circular holes (35) shown in FIGS. 5-7 are provided for exemplary purposes and that the present invention is not limited to such. Specifically, any other means known in the art may be utilized to rotatably secure the semi-elliptical movable locking member (36a, 36b) to the respective cervical link (30a, 30b), such as a screw, bar, pin, bolt or the like.

The semi-elliptical movable locking member 36 includes a semi-elliptical knob having elongated portions that are configured for frictional engagement with other components of the cervical link system 10 (as detailed below) when the knob is rotated into a locked position.

Each cervical link (30a, 30b) is secured to a vertebral body of a patient, by one or more screws (38a-38d) or the like, which are projected through the circular holes (34a, 34b). The connecting assembly 40 is arranged to be inserted into the center recessed portion 34 along each outer semi-elliptical side wall of the center recessed portion 34 of each cervical link (30a, 30b). The generally semi-circular cross-section of the circular recessed portions (16a, 16b) is configured and sized to receive the connecting assembly 20. The semi-elliptical movable locking member 36 is arranged such that the connecting assembly 40 is frictionally engaged between the outer semi-elliptical side wall of the center recessed portion 34 and the semi-elliptical movable locking member 36 when the semi-elliptical knob of the semi-elliptical movable locking member 36 is rotated such that the elongated portions force the connecting assembly 40 in an outward direction towards the outer semi-elliptical side wall of the center recessed portion 34.

Optionally, semi-elliptical movable locking member 36 may include one or more positioning holes shown to the right and left of its center position. As shown in FIG. 6, exemplary non-limiting countersunk screws (37a, 37b) can be tightened after the knob is rotated into a locked position. The positioning holes may be optionally used by a tool for the purpose of assisting in rotating the knob into a locked position.

During surgery, a vertebral body or disc of a patient is approached anteriorly. An incision is made on the front of the neck, off to the side. The trachea and esophagus are retracted out of the way thereby exposing the vertebral body or disc of the patient. The disc is then removed which decompresses the spinal cord and nerve roots. After the disc is removed, a graft is placed at that location along the vertebral spine of the patient. The graft can be the patient's own bone, but more often is cadaveric bone or a PEEK cage (form of plastic). The type of graft usually depends on surgeon preference. After the graft is placed a cervical link (12a, 12b or 30a, 30b) is selected and screwed into the vertebral body above and below the graft. It is not uncommon to have more than one disc removed during the ACDF.

After the cervical links (12a, 12b or 30a, 30b) are attached to the vertebral bodies, the cervical links (12a, 12b or 30a, 30b) are connected by means of frictional engagement (as described above) with the connecting assembly 40.

Although an exemplary embodiment of the system of the present invention has been illustrated in the accompanied drawings and described in the foregoing detailed description, it will be understood that the invention is not limited to the embodiments disclosed, but is capable of numerous rearrangements, modifications, and substitutions without departing from the spirit of the invention as set forth and defined by the following claims. Still further, although depicted in a particular manner, any number of modules and connections can be utilized with the present invention in order to accomplish the present invention, to provide additional known features to the present invention and/or to make the present invention more efficient.

Obviously, many other modifications and variations of the present invention are possible in light of the above teachings. The specific embodiments discussed herein are merely illustrative, and are not meant to limit the scope of the present invention in any manner. It is therefore to be understood that within the scope of the disclosed concept, the invention may be practiced otherwise than as specifically described.

What is claimed is:

1. An adjustable cervical link system comprising:
    a plurality of cervical links that include:
        at least one hole to receive a fastener for securing the cervical link to a respective article of a patient's cervical spine;
        a recessed portion forming two separate curved side walls across the cervical link, and each curved side wall is curved in at least two separate planes; and
        a locking member having two ends positioned opposite to each other at a longest cross dimension and having an elliptical shape, the locking member disposed and rotatable in the recessed portion such that the two ends minimize a gap toward the two curved side walls of the recessed portion of the cervical link at some relative orientations; and
    a connecting assembly configured to be held between the two ends of the locking member and the corresponding curved side walls of at least two of the plurality of cervical links via a friction fit between the two ends positioned opposite to each other at the longest cross dimension to secure a relative position and orientation of the plurality of cervical links fastened to the patient's cervical spine, wherein the connecting assembly is releaseable from one or more of the plurality of cervical links when corresponding locking members are rotated in the recessed portion of the one or more of the plurality of cervical links.

2. The adjustable cervical link system of claim 1, wherein the article of the patient's cervical spine includes a vertebral body of the patient.

3. The adjustable cervical link system of claim 1, wherein the locking member includes two or more cavities for receiving a tool that transmits a torque to rotate the locking member to position the connecting assembly between the curved side walls and the ends of the locking member.

4. The adjustable cervical link system of claim 1, wherein the locking member has two rounded ends.

5. The adjustable cervical link system of claim 1, wherein the locking member is fastened onto one of the plurality of cervical links at a center of both the locking member and the one of the plurality of cervical links, and wherein the locking member is rotatable around a second fastener.

6. The adjustable cervical link system of claim 1, wherein the minimized gap between one of the ends of the locking member and one of the two curved side walls has a cross sectional profile the same as a cross sectional profile of the connecting assembly.

7. The adjustable cervical link system of claim 6, wherein the locking member at least partially elastically deforms the connecting assembly to result in the friction between the connecting assembly and the two curved side walls and the two ends.

8. The adjustable cervical link system of claim 1, wherein the two ends positioned opposite to each other at the longest cross dimension of the locking member are configured to extend past of the recessed portion when the locking member is not engaged with the connecting assembly.

9. An adjustable cervical link system comprising:
    a plurality of cervical links for fixation to articles of a patient's cervical spine, wherein the plurality of cervical links has a plurality of holes arranged to receive a fastener thereby securing the plurality of cervical links to the respective article of a patient's cervical spine, and wherein the plurality of cervical links has a recessed portion formed within a top portion of the plurality of cervical links, the recessed portion forming two separate curved side walls across the cervical link and each curved side wall is curved in at least two separate planes;
    one or more center members positioned adjacent the recessed portion formed within the top portion of the plurality of cervical links; and
    a connecting assembly having an open interior defined by one or more interior surfaces of the connecting assembly, wherein at least a portion of the connecting assembly is configured to be retained within at least a portion of the recessed portion formed within the top portion of one or more of the plurality of cervical links, wherein the center members are operable to occupy at least a portion of the open interior of the connecting assembly,
    wherein the center member of at least one of the plurality of cervical links comprises an elliptical adjustment member that is rotatable within the recessed portion between locked and unlocked positions, wherein when in the locked position the elliptical adjustment member engages one of the one or more interior surfaces of the connecting assembly at a desired position of the connecting assembly via a friction fit to retain the at least one of the plurality of cervical links in a first position along the length of the open interior of the connecting assembly, and wherein when in the unlocked position the elliptical adjustment member is spaced apart from the connecting assembly such that the connecting assembly is not retained by the at least one of the plurality of cervical links, and
    wherein the engaged interior surface of the connecting assembly is transverse to the length of the open interior of the connecting assembly.

10. The adjustable cervical link system of claim 9, wherein the portion of the connecting assembly is retained within at least the portion of the recessed portion via the friction fit provided by the elliptical adjustment member at an opening of the recessed portion, the opening having a width less than a width of the retained portion of the connecting assembly at the friction fit of the elliptical adjustment member.

11. The adjustable cervical link system of claim 9, wherein the one or more interior surfaces of the connecting assembly form a rectangular shape defining the open interior.

12. A cervical link comprising:
- a body having a thickness and a width, the body including two or more holes to receive respective fasteners;
- a recess portion at a center of the body, the recess portion forming two separate curved internal side walls have a height less than the thickness, each of the two separate curved internal side walls are curved in at least two separate planes; and
- a locking member disposed and rotatable at least partially inside the recess portion, the locking member having two ends positioned opposite to each other at a longest cross dimension and having an at least partially elliptical shape, the locking member disposed and rotatable at least partially in the recessed portion such that the two ends minimize a gap toward the two curved side walls of the recessed portion of the cervical link at some relative orientations, such that the locking member is rotated and configured to position a portion of a connecting assembly between the curved side walls and the ends of the locking member via a friction fit between the two ends positioned opposite to each other at the longest cross dimension.

13. The cervical link of claim 12, wherein the locking member is rotatably fastened to a center of the recess portion and the center of the body.

14. The cervical link of claim 12, wherein the connecting assembly holds two or more of the cervical links to secure a spine of a patient.

15. The cervical link of claim 12, wherein the locking member includes one or more cavities for receiving a tool that transmits a torque to rotate the locking member.

16. The cervical link of claim 12, wherein the minimized gap between one of the rounded ends of the locking member and one of the two curved side walls has a cross sectional profile the same as a cross sectional profile of the connecting assembly.

17. The cervical link of claim 12, wherein the locking member at least partially elastically deforms the connecting assembly to result in the friction between the connecting assembly and the two curved side walls and the two ends.

* * * * *